United States Patent
Lee et al.

[11] Patent Number: 6,159,375
[45] Date of Patent: *Dec. 12, 2000

[54] METHOD FOR REMOVING LEUKOCYTES AND METHYLENE BLUE FROM PLASMA

[75] Inventors: Eric Kin-Lam Lee, Acton; Yves Fouron, Marlborough; Franco Castino, Sudbury; Charles Melvyn Zepp, Berlin, all of Mass.

[73] Assignee: Hemasure, Inc., Marlborough, Mass.

[*] Notice: This patent is subject to a terminal disclaimer.

[21] Appl. No.: 09/371,141

[22] Filed: Aug. 9, 1999

Related U.S. Application Data

[60] Continuation of application No. 08/862,517, May 23, 1997, Pat. No. 5,935,436, which is a division of application No. 08/347,564, Nov. 30, 1994, Pat. No. 5,639,376, which is a continuation-in-part of application No. 08/204,102, Mar. 1, 1994, abandoned, which is a continuation-in-part of application No. 08/179,567, Jan. 10, 1994, abandoned.

[51] Int. Cl.[7] .......................... B01D 37/00; B01D 39/02; B01D 39/04
[52] U.S. Cl. .......................... 210/645; 210/694; 436/177
[58] Field of Search .................... 210/490, 505, 210/508, 645, 694, 767, 435, 488, 489, 503; 435/2; 422/101; 436/177, 178, 528, 529, 530, 531; 530/412, 413

[56] References Cited

U.S. PATENT DOCUMENTS

| | | | |
|---|---|---|---|
| 4,246,107 | 1/1981 | Takenaka et al. | 210/806 |
| 4,283,289 | 8/1981 | Meyst et al. | 210/448 |
| 4,358,376 | 11/1982 | Moriuchi et al. | 210/282 |
| 4,416,777 | 11/1983 | Kuroda et al. | 210/446 |
| 4,693,985 | 9/1987 | Degen et al. | 436/531 |
| 4,880,548 | 11/1989 | Pall et al. | 210/767 |
| 4,923,620 | 5/1990 | Pall | 210/767 |
| 4,925,572 | 5/1990 | Pall | 210/767 |
| 4,936,998 | 6/1990 | Nishimura et al. | 210/638 |
| 5,152,905 | 10/1992 | Pall et al. | 210/767 |
| 5,190,657 | 3/1993 | Heagle et al. | 210/645 |
| 5,256,532 | 10/1993 | Melnicoff et al. | 435/5 |
| 5,591,350 | 1/1997 | Piechocki et al. | 210/503 |

FOREIGN PATENT DOCUMENTS

| | | |
|---|---|---|
| 63391/90 | 4/1991 | Austria . |
| 239859 | 10/1987 | European Pat. Off. . |
| 0341413 | 11/1989 | European Pat. Off. . |
| 397403 | 11/1990 | European Pat. Off. . |
| 478914 | 4/1992 | European Pat. Off. . |
| 4021542 | 1/1992 | Germany . |
| 2167071 | 6/1990 | Japan . |

OTHER PUBLICATIONS

Klein, Blood, vol. 80, pp. 1865–1867, 1992.
Beutler et al., J. Lab. Clin. Med., vol. 88, pp. 328–333, 1976.
Hou et al., Artif. Organs, vol. 14, pp. 436–442, 1990.
Horowitz et al., Transfusion, vol. 25, pp. 516–522, 1985.

*Primary Examiner*—John Kim
*Attorney, Agent, or Firm*—Heslin & Rothenberg, P.C.

[57] ABSTRACT

Filter devices for simultaneously removing leukocytes and viral inactivating agents from whole blood or blood fractions are disclosed. One type of device comprises (1) a housing surrounding (2) activated carbon and (3) a mechanically stable polymeric material which may optionally be modified to attach a ligand for leukocytes. General methods for removing leukocytes and viral inactivating agents from blood and plasma are also disclosed.

12 Claims, 2 Drawing Sheets

METHOD FOR REMOVING LEUKOCYTES AND METHYLENE BLUE FROM PLASMA

CROSS-REFERENCES TO RELATED APPLICATIONS

This is a continuation of U.S. application Ser. No. 08/862,517, filed May 23, 1997, U.S. Pat. No. 5,935,436, which is itself a divisional of U.S. application Ser. No. 08/347,564, filed Nov. 30, 1994, U.S. Pat. No. 5,639,376, which is itself a continuation-in-part of our copending U.S. application Ser. No. 08/204,102, filed Mar. 1, 1994, abandoned, which is a continuation-in-part of our earlier copending application Ser. No. 08/179,567, filed Jan. 10, 1994, abandoned, the entire disclosures of which are incorporated herein by reference.

FIELD OF THE INVENTION

The invention relates to filters for removing leukocytes and viral inactivating agents from whole blood or blood fractions, and methods for using the filters to remove leukocytes and viral-inactivating agents from whole blood or blood fractions.

BACKGROUND OF THE INVENTION

A significant risk associated with the use of blood products in transfusion medicine is the presence of viruses in such products as whole blood, plasma, platelets, and various blood fractions. A number of chemicals have been identified as viral inactivating agents; their addition to the blood product, sometimes in conjunction with irradiation by visible and/or ultraviolet light, causes viruses to lose their infectivity. For example, methylene blue is added to plasma intended for transfusion. Although methylene blue exhibits effective virucidal activity and is considered generally safe, it nevertheless represents an exogenous component in the plasma with possible long-term adverse effects not yet fully understood. Other viral inactivation agents such as psoralens carry similar risks. One object of the present invention is to offer a method for removing antiviral agents after their virucidal function is completed.

European application 239,859 describes a method that is currently employed to remove lipid soluble process chemicals from biological fluids. It comprises bringing the fluid into contact with a naturally occurring oil, agitating the resultant mixture, separating the phases by sedimentation or centrifugation, decanting the upper lipid phase, and utilizing the residual biological fluid. Aside from the mechanical complexity of this process, it appears applicable only to the removal of lipid soluble process chemicals.

Gel filtration is also known for removing small molecules from blood fractions based on molecular weight differences. Horowitz et al. [*Transfusion*, 25, p. 516–522 (1985)] have described the removal of tri-n-butyl phosphate from anti-hemophilic factor concentrates by chromatography on Sephadex G-25; however, gel chromatography is not a practical method for removing small molecules from plasma and whole blood.

PCT application WO 91/03933 discusses the use of silica gel, modified silica gel, glass beads, and amberlite resins to adsorb methylene blue from plasma. None of the methods presently in use or proposed is particularly attractive for the routine processing of plasma.

A second concern that arises with blood products, including those such as plasma, is their non-homogeneity; blood products commonly include several cell types as well as a variety of molecular components having differing biological activities. Often patients into whom the blood product is to be transfused are only in need of one component, and the other components present in the blood product are not only unnecessary but may even be disadvantageous or harmful. In this respect, leukocytes have come to be regarded as unwanted passengers in transfusions because "once transfused, they may turn upon their host and unleash endogenous pyrogens, cell-associated viruses, or even lethal graft-versus-host disease." [see Klein "Wolf in Wolf's Clothing: Is It Time to Raise the Bounty on the Passenger Leukocyte?" *Blood* 80, 1865–1867 (1992)]. For this reason it is desirable that leukocytes be reduced to the lowest feasible levels. It would therefore be highly desirable to have a method for removing leukocytes from plasma quickly and efficiently. Moreover, there is a need for a simple and effective method for simultaneously removing viral inactivating agents and leukocytes from plasma.

Media and devices for removing leukocytes from red blood cell concentrates, platelet concentrates, and other blood fractions have been described. The media are typically non-woven mats of controlled fiber diameter. They are adequate as components for fabricating a device according to the invention, but media for filtration based primarily on separation by size can be improved by adding ligands for leukocytes, as described in our earlier copending application Ser. No. 08/179,567.

SUMMARY OF THE INVENTION

It is an object of the present invention to provide a filter for removing both leukocytes and viral inactivating agents (such as methylene blue and its metabolites and photodecomposition products) from plasma or other blood fractions quickly, safely and with very high efficiency.

It is a further object to provide a method of removing leukocytes and viral inactivating agents from whole blood, plasma or other blood fractions. It is an advantage of the invention that the foregoing objects can be accomplished quickly, thoroughly and inexpensively.

The present invention permits efficient, integrated (i.e., single-step) removal of both leukocytes and virus-inactivating compounds from plasma—thus producing a blood product free of active viruses, antiviral compounds, and leukocytes.

These and other objects, features and advantages are realized by the present invention which relates to a method for simultaneously removing leukocytes and one or more viral inactivating agents from blood products, such as plasma. The method comprises passing the plasma through a filter adapted for removing leukocytes and antiviral agents. "Adapted for removing leukocytes" means having appropriate geometry and surface chemistry to trap at least a portion of available leukocytes while allowing other blood components of interest to pass. Removal of antiviral agents is achieved by means of sorption onto activated carbon or media containing activated carbon.

In one aspect the invention relates to a method for simultaneously removing leukocytes and one or more viral inactivating agents from whole blood or a blood fraction comprising passing the blood or blood fraction through a filter adapted for removing leukocytes and antiviral agents, said filter comprising (1) a mechanically stable polymeric material capable of retaining leukocytes and (2) activated carbon capable of removing the viral inactivating agent. A portion of the mechanically stable polymeric material may optionally have covalently attached thereto a first ligand, which has affinity for a leukocyte cell surface. In a preferred method, the blood fraction is plasma. In another preferred method pertaining specifically to plasma, the viral inactivating agent is selected from the group consisting of phenothiazine dyes and photodecomposition products of phenothiazine dyes. Preferably, the viral inactivating agent is selected from the group consisting of methylene blue, toluidine blue, and photo-decomposition products of methylene blue and toluidine blue. The mechanically stable polymeric material that retains leukocytes may be included within a laid textile web.

In a specific embodiment, the blood or blood fraction is passed sequentially through (1) a layer containing activated carbon and (2) at least one shape-sustaining laid textile web having a thickness of 1 to 8 mm and a bulk density of 0.05 to 0.4 g/cm$^3$. The web is made up of:

(a) a plurality of interlocked textile fibers with average deniers between 0.05 and 0.75 and average lengths between 3 mm and 15 mm. The textile fibers are substantially uniformly distributed in the web so as to form a matrix of the textile fibers with spaces between adjacent interstices of interlocked fibers; and (b) a mechanically stable polymeric material comprising a plurality of fibrillated particles of polymeric material having a surface area of 5 to 60 square meters per gram substantially disposed within the spaces of the matrix. The fibrillated particles have a plurality of fine fibrils which are interlocked with adjacent textile fibers of the spaces such that the fibrillated particles are not substantially displaceable from the web during filtration.

In another aspect the invention relates to a filter device for removing leukocytes and one or more viral inactivating agents from whole blood or a blood fraction, comprising (1) a housing, enclosing (2) an activated carbon-containing filter element and (3) at least one filter element adapted for retaining leukocytes. The filter element for retaining leukocytes may comprise a laid textile web which may optionally include a mechanically stable polymeric material having attached thereto a first ligand, which has affinity for the leukocyte cell surface. The first ligand may be attached directly to the polymeric material, or it may be attached to the polymeric material through at least one intervening linker. When present, a preferred ligand is heparin.

In a specific embodiment, the filter device comprises (1) an activated carbon-containing filter element, preferably a carbon/cellulose composite, and (2) a shape-sustaining laid textile web as described above wherein the weight ratio of the fibrillated particles to the textile fibers is between 1:99 and 40:60. A preferred polymeric material is cellulose acetate and preferred textile fibers are polyolefin and polyester fibers.

DETAILED DESCRIPTION INCLUSIVE OF PREFERRED EMBODIMENTS

Figure 1:
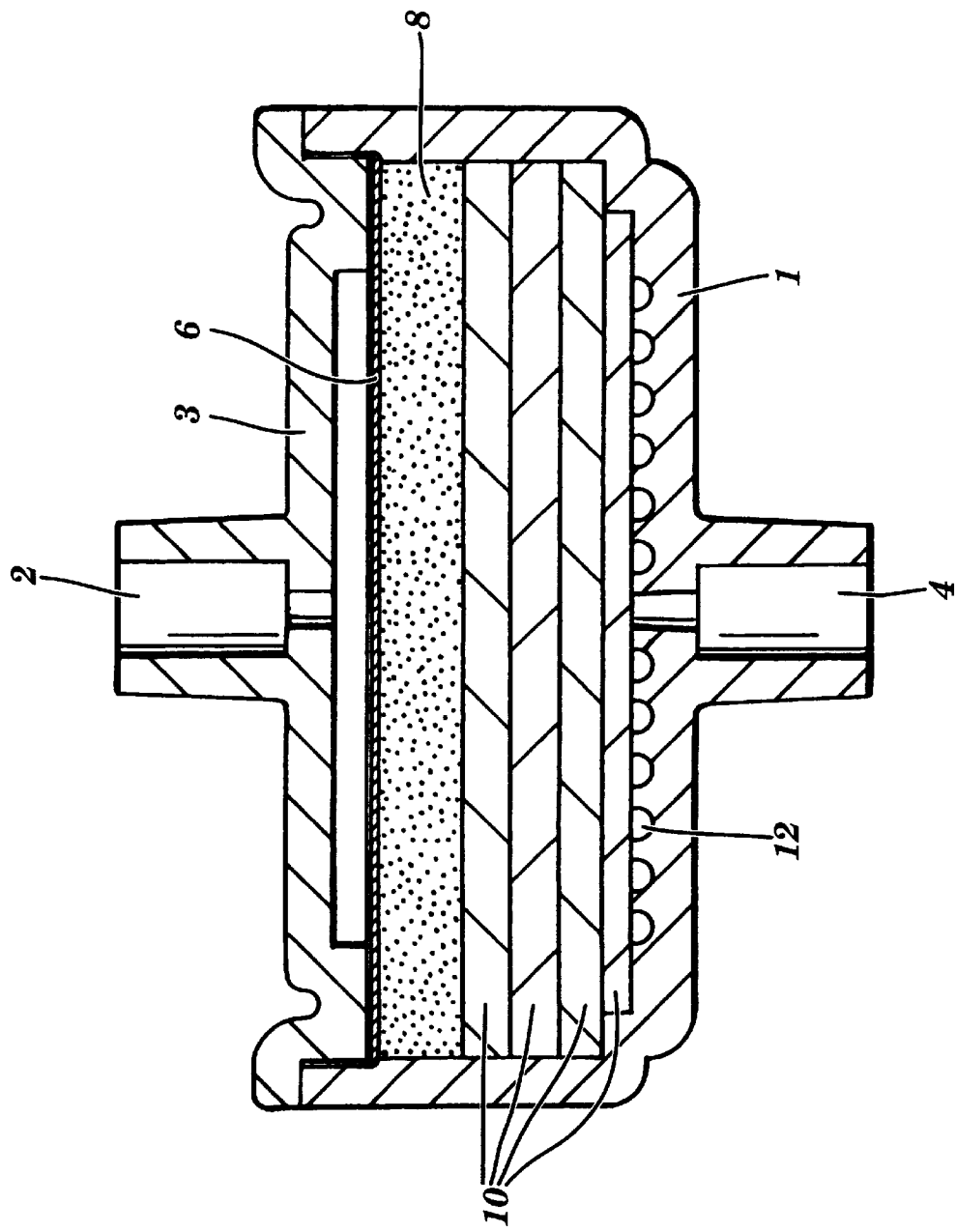
FIG. 1 is a diagrammatic cross-sectional view of a filter device according to the invention.

In recent years there has been great interest in inactivating viruses such as Hepatitis B (HBV), Hepatitis C (HCV), Human T Lymphotrophic Retrovirus Type 3 (HTLV), Human Immunodeficiency Virus (HIV), and Lymphadenopathy Associated Virus (LAV) in blood and blood products. At present, methods for inactivating these viruses in blood and blood fractions include treatment with a chemical disinfectant such as formaldehyde (see U.S. Pat. No. 4,833,165); treatment with solvents and detergents (see U.S. Pat. No. 4,540,573) and treatment with photosensitizers. For example, U.S. Pat. No. 5,232,844 describes the use of phthalocyanines; U.S. Pat. No. 5,041,078 describes the use of sapphyrins; U.S. Pat. Nos. 4,169,204, 4,294,822, 4,328,239 and 4,727,027 describe the use of various furocoumarins (psoralens) and analogs thereof; Meruelo et al. [*Proc. Nat. Acad. Sci. U. S.*, 85, 5230–5234 (1988)] have described the use of hypericin; Lambrecht et al. [*VOX Sang.* 60, 207–213 (1991)] and Mohr and Lambrecht [PCT application WO 91/03933] have described the use of phenothiazine dyes (methylene blue and toluidine blue); and U.S. Pat. No. 4,915,683 describes the use of merocyanine dyes to inactivate viruses. According to these methods, an exogenous photosensitizer is added to the blood or plasma and the solution is irradiated with light of appropriate wavelengths to inactivate the virus.

Phenothiazine dyes are photochemicals that bind to nucleic acids. Under suitable activation conditions such as long-wavelength UV irradiation, phenothiazine dyes crosslink the DNA and RNA strands in viruses, thereby disabling uncoiling and replication. They also react with membrane structures and they induce the production of virucidal oxygen radicals from molecular oxygen. These characteristics of phenothiazine dyes form the basis of viral inactivation and certain photochemotherapies. [See PCT application WO 91/03933.] However, the slight excess of phenothiazine dyes used to ensure thorough interaction with viruses and the consequent residue left in the plasma represents some risk to the patient upon transfusion. For example, methylene blue has been suggested to possess a certain level of mutagenicity and other adverse effects may become of concern with long-term exposure associated with regular transfusion. It is therefore desirable to remove the unreacted phenothiazine dyes or their metabolites and photodegradation products from the plasma after the viral inactivation treatment.

In all of the antiviral treatments, exogenous agents are added to the biological fluid. In most cases, these exogenous agents must be removed from the biological fluid before it can be administered to a human. The present invention entails the perfusion of the biological fluid through an appropriately sized filter, which captures both leukocytes and viral inactivating agents. In some embodiments the filter may be designed to enhance the removal of leukocytes through the use of a matrix which is surface treated with carbohydrate-based ligands.

In the case of phenothiazine dyes used as the viral inactivating agents, single donor units of plasma are individually injected with precisely measured amounts of the dye, and mixed thoroughly inside the blood bag, The entire blood bag is then irradiated with fluorescent light or narrow-band red light from light emitting diodes for a prescribed period of time. This practice is fundamentally different from the batchwise treatment of pooled plasma, i.e. large volumes of plasma obtained by combining many single-donor units. Pooling is convenient from a processing scale viewpoint, but has the disadvantage that a single infected unit of plasma, ie. one carrying pathogens, is capable of contaminating an entire plasma pool. Single-donor unit processing avoids this risk; the practice is also particularly suited for subsequent viral inactivating agent removal with an individual, disposable filtration device to result in a higher quality, individually identifiable unit of plasma.

A filtration device may be sized according to the quantity of treated plasma requiring methylene blue removal. Preferably, the device is designed to remove essentially all of the viral inactivation agent used to treat a single unit of plasma—a highly desirable practice rendered feasible by the methylene blue technique, for example.

In this invention, plasma that has been viral inactivated with methylene blue is brought into contact with a filter medium containing activated carbon in a flow-through device. The activated carbon may be in the form of a discrete sorption layer of powder, granules, fibers, or fabric (woven, knitted, or nonwoven). Alternatively, carbon fibers (filaments or staples) may be incorporated into a filter matrix as one of its components. Another medium may be a porous solid comprising activated carbon as its active ingredient. Yet another medium may be a composite structure, combining one or more forms of activated carbon with other non-carbonaceous structural elements, to provide filtration media with specific sorption, permeability and mechanical properties. In all cases, sorption of methylene blue will take place primarily on the activated carbon surfaces.

In the flow path of the filter device, the activated carbon medium may be preceded by a depth filter with the capability of removing lipids and solid impurities which may be present. Alternatively, the activated carbon medium itself may be constructed so as to impart lipid and solid retention properties. Another filter may optionally be placed downstream of the activated carbon media to retain fragments or particles that may be released from any of the filter components.

A hydrophilic coating may optionally be applied to the activated carbon surfaces. This coating serves one or more of the following functions: 1) to encapsulate and contain the carbon material, thus reducing release of fine particulates into the filtered plasma; 2) to reduce undesirable interaction between the activated carbon and plasma components by offering a biocompatible surface in direct contact with the plasma; and/or 3) to reduce or prevent sorption of species substantially larger than methylene blue by means of size exclusion, viz. allowing relatively unimpeded permeation of methylene blue and photolytic products compared to that of larger molecules. The "cutoff" molecular weight of the species to be excluded may be controlled by varying the composition of the encapsulating layer. This is a method of reducing binding of desirable proteinaceous components in the plasma, such as coagulation factors, by the activated carbon. Similar considerations apply to the removal of viral inactivation agents other than phenothiazine dyes.

Plasma samples, especially those collected as single-donor units, exhibit a range of properties, the most readily noticeable of which is the presence of chylomicrons. Chylomicrons include a range of lipid species of different sizes and degree of agglomeration. Units of plasma heavily laden with chylomicrons become more noticeably tinted by methylene blue because of preferential sorption of the dye by the lipid, and are correspondingly more objectionable to the user. In addition, such units are more challenging to filter because they tend to clog the pores of filter media.

To reduce the effect of clogging and ensure filtration of a single-donor unit of plasma can be completed within a reasonable time requires that sufficient frontal area be available in the filter. This influences the design of the filter device in terms of packaging the necessary quantity of sorption media into the most favorable aspect ratio, i.e. the ratio of frontal surface area to volume. The filter media may be shaped as layers of flat sheets, or as hollow fibers or cylinders where the plasma flow would be directed through their annular walls.

Activated carbon media offer the advantage of a high-capacity sorbent, which translates to compact filter devices with small holdup volumes, and thus high recovery of the plasma product. With specific grades of activated carbon and/or by applying surface coatings, selective sorption properties may be created to allow removal and retention of different target components in the treated plasma.

To minimize risks associated with repeated transfusion in long-term therapy, it is prudent to remove as much methylene blue and its photoreaction byproducts (e.g. Azure B, Azure C) as possible after the viral inactivation step, preferably to levels below detectability (ca. 0.02 $\mu$g methylene blue/mL plasma). An example of a suitable medium for this purpose is a carbon composite medium in which activated carbon particles are uniformly dispersed and embedded in a cellulose fibrous matrix.

Much of the methylene blue added to plasma becomes associated with the chylomicron or endogenous lipids. Effective clearance of the dye from the plasma therefore also requires simultaneous removal of this lipid fraction. In addition, effective lipid removal would enable excessively lipemic plasma units previously rejected to be processed for transfusion. A fibrous, porous matrix made of lipophilic (i.e. hydrophobic) materials is appropriate for removing plasma lipids. Since removal is accomplished by adsorption and size exclusion mechanisms, preferred media include those with relatively high surface area-to-volume ratios, morphologies favorable to depth filtration (e.g. decreasing effective pore diameter in the direction of flow through the thickness of the filter), and good biocompatibility to prevent excessive non-specific protein adsorption.

Various coagulation factors may be depleted by non-specific adsorption on the filter media. The consequences vary. For example, loss of Factor VIII is less significant than a comparable loss of Factor V, because the former may be replenished using commercially available plasma fraction preparations, while the latter is not. An ideal filter device should minimize changes in coagulation factor content of the plasma before and after filtration. In practice, some modest degree of removal of coagulation factors may be tolerated because an excess of such factors is present in the human body, and because the volume of plasma transfused typically represents a small fraction of the total plasma volume in the circulatory system.

Platelet-poor plasma used for transfusion typically has a leukocyte burden of about $10^6$ per mL. A 3-log reduction to 1 per mL is generally considered adequate for transfusion purposes. With the device and method of the invention, leukodepletion may be performed simultaneously with methylene blue removal after methylene blue treatment. Leukodepletion after methylene blue treatment allows both the plasma-borne and leukocyte-borne viruses to be inactivated simultaneously. Studies have shown that a methylene blue concentration of 0.1 $\mu$M is adequate for both purposes.

There is some evidence that platelets may be activated by contact with carbon particles. This problem may be addressed effectively in two ways: by coating the carbon surface with a more biocompatible material as discussed above, or by removing the platelets altogether from the plasma by sorption onto appropriate depth filter media.

The filter comprises (1) a mechanically stable polymeric material, which may have a surface chemistry adapted for removing leukocytes, and (2) activated carbon or a medium containing activated carbon for removing viral inactivating agents. In one embodiment, at least a portion of the mechanically stable polymeric material has covalently attached a first ligand having affinity for the leukocyte cell surface.

A suitable leukocyte depleting medium for use in the device of the invention may comprise a laid textile web which includes a mechanically stable polymeric material. In an improved medium, a portion of the polymeric material may optionally have covalently attached thereto a first ligand, which has affinity for a leukocyte cell surface. In one embodiment, the first ligand may be attached directly to the polymeric material; in another, the first ligand is attached to the polymeric material through at least one intervening linker.

The first ligand may be a glycoprotein of the selectin family, or a carbohydrate, particularly a sulfoglycan that includes residues of glucuronic acid, such as a heparin. The intervening linker may be the residue of an alkylene diamine, in which case, the linker may be attached to the ligand by an amide bond to a carboxyl of the ligand, when one is present.

In the case of heparin, chondroitin sulfate and similar glycans bearing carboxylic acid residues, the carboxylic acid may be activated for reaction with a nucleophile in the linker or polymeric material. Usually the nucleophilic residue is a primary amine and the activation utilizes any of the procedures well known in the art for forming amide bonds. We have found that EEDQ and 1-ethyl-3-(3-dimethylaminopropyl) carbodiimide (EDC) are particularly useful.

Other ligands now known or subsequently discovered are expected to function similarly. The critical requirements of the leukocyte ligand are a high affinity for the leukocyte surface and a functionalizable substituent at some position remote from the binding region whereby the ligand can be covalently bound to the polymeric material.

In operation, an individual unit of plasma (or if necessary, some larger volume of plasma being processed) that is suspected of being contaminated by a virus will be treated by the addition of an effective concentration of a virus-inactivating phenothiazine dye to the plasma. The unit of plasma is then irradiated for a sufficient time to permit the antiviral compound to inactivate both "free" (i.e., plasma-borne) and cell-associated virus.

Next, and involving the methods and devices of the present invention, the treated plasma, still containing at least significant amounts of antiviral agent, will be passed through the leukocyte/antiviral filter of the present invention, to produce a plasma product substantially free of active viruses, leukocytes capable of harboring them, and residuals of the antiviral compound itself.

Filters that can remove leukocytes are known in the art. For example, Lydall Inc. manufactures a suitable leukodepletion filter, and Asahi Chemical manufactures another. More efficient filters activated by attachment of heparin and other ligands capable of enhancing the capture of leukocytes are disclosed in our earlier, copending U.S. application Ser. No. 08/179,567, abandoned.

One filter element useful in the fabrication of the filter of the present invention is a modification of the filter described in U.S. Pat. No. 5,190,657, the disclosure of which is incorporated herein by reference. Briefly, the filter consists of a filter material which is a shape-sustaining laid textile web. The web will commonly be cut in a circular configuration to form the filter and is suitable for loading into a cylindrical filter carrier.

The thickness of the web is at least 1 millimeter, most preferably at least 2 millimeters, and can be up to about 8 mm. The density of the laid web is between about 0.05 and 0.4 g/cm³.

The filter material is comprised of a plurality of matrix textile fibers, and these textile fibers have average deniers between about 0.05 and 0.75. At least 60%, preferably at least 70% and more preferably at least 80 to 85% of the fibers have deniers within the above-noted ranges, and lengths from 12,000 to 180,000 m/g. The textile fibers are substantially uniformly distributed through the web so as to form a matrix of the textile fibers. The matrix has spaces between adjacent interstices of the interlocked fibers. Within these spaces, there are a plurality of fibrillated particles of very high surface area. The fibrillated particles are disposed within spaces, as well as along and among the matrix textile fibers.

The matrix textile fibers are commonly synthetic polymer fibers, such as polyolefin or polyolefin-sheathed fibers, polyamide, polysulfone, polyester, polyvinyl alcohol and poly(ethylene-vinyl alcohol) copolymer fibers. Polyolefin fibers are preferred.

The fibrillated particles are polyester fiber material, acrylic fiber material, nylon fiber material, polyolefin fiber material or cellulosic fiber material. Cellulose acetate is usually used since a great number of fibrils are produced with that material, and the material has a natural hydrophilic nature.

Figure 2:
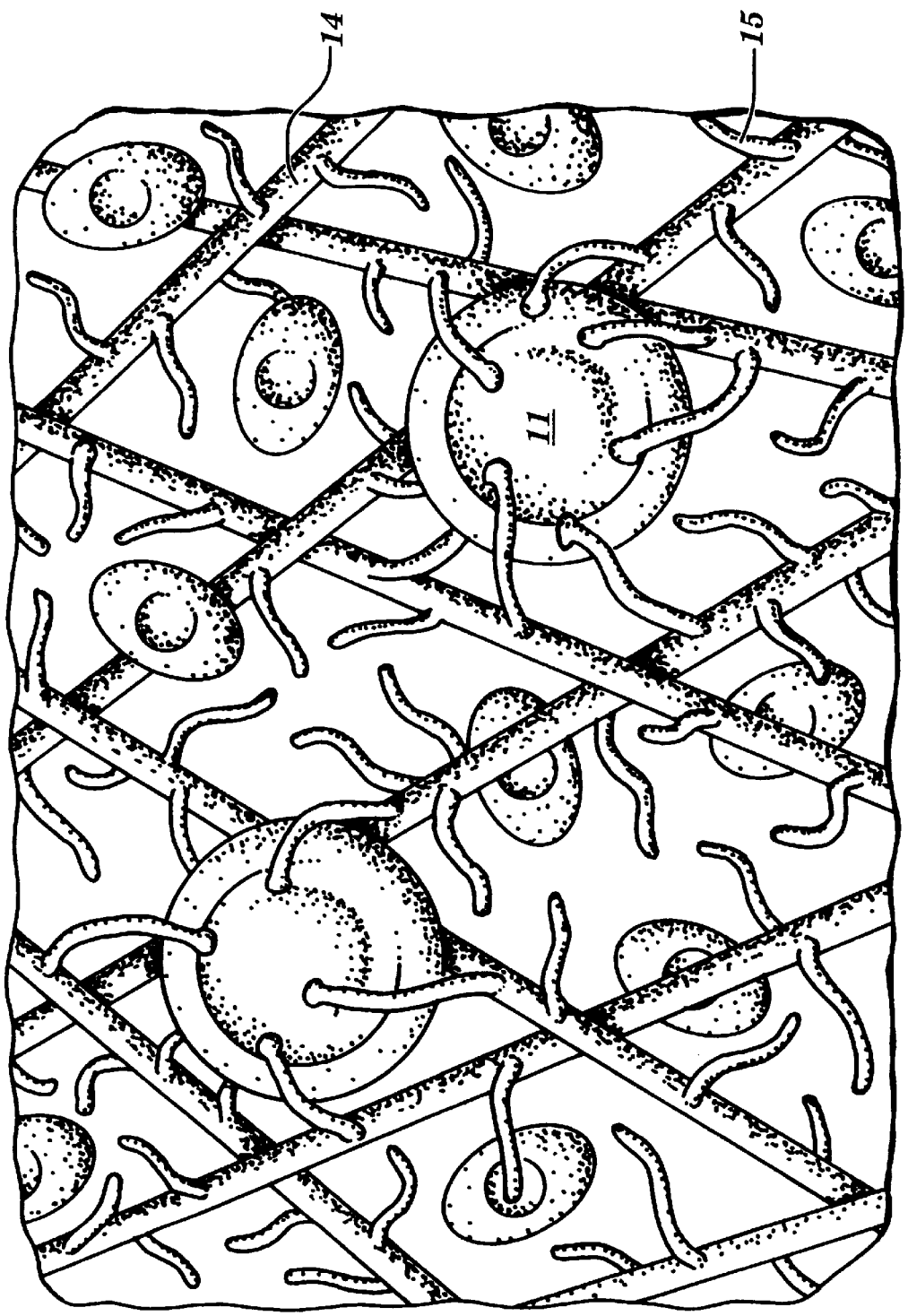
FIG. 2 is a schematic representation of a filter medium according to the disclosure of parent application Ser. No. 08/179,567, abandoned, showing attached ligands for leukocyte surface features.

FIG. 2 illustrates, in a highly idealized schematic form, one embodiment of a filter element useful in the filter of the present invention. The filter is comprised of a polymeric material 14 to which are covalently bonded a plurality of ligands 15 for leukocyte cell surface features. In use, the leukocytes 11 are held within the filter matrix both by mechanical effects (size) and by specific interactions between binding sites on the ligands 15 and sites on the surface of the leukocytes.

The filter elements used in the examples that follow are commercially available from Lydall Inc. [Hamptonville, N.C.] and consist of polypropylene fibers and fibrillated cellulose acetate "fibrets." In general, any filter comprised of a cellulose acetate component and a shape-sustaining web that is resistant to base hydrolysis will function in the methods described in application Ser. No. 08/179,567, abandoned, for preparing surface-modified filters, or may be used directly as a leukodepletion medium without further modification.

The particular filter device described below as a preferred embodiment has the additional feature that it also removes chylomicrons, microaggregates, bacteria and endotoxins from plasma. The combined effects of the various features of the device are quite profound: (a) By removing>95% of methylene blue and its photolysis products, it eliminates concern about methylene blue toxicity and concern about the visual appearance of the plasma; (b) by removing>99.9% of leukocytes, it improves virus inactivation capability, reduces leukocyte-associated bacteria (e.g. *Yersinia histolytica*), and reduces leukocyte-associated immunologic effects; (c) by removing chylomicrons or lipids it improves the appearance of the plasma, eliminates the need for a microaggregate filter at the bedside, and avoids having to discard highly lipemic plasma units; (d) by removing bacteria, it reduces sepsis; and (e) by removing endotoxins, it reduces or eliminates febrile reactions. All of these advantages are accomplished at low cost, with a plasma volume loss of less than 5%, and the process can be carried out on a single donor unit basis, thereby avoiding the hazards associated with pooling blood supplies.

EXAMPLES

A series of devices have been developed which incorporate multiple functions described above. These were evaluated for several key performance criteria; extent of methylene blue removal, time for filtering a unit of plasma (the volume of a unit of single-donor plasma may vary from 200 to 300 mL), extent of leukodepletion and the effect of this filtration on the extent of depletion of various coagulation factors.

The filter device shown in FIG. 1 consists of a cylindrical housing 1 and cover 3 fitted with inlet 2 and outlet 4 tubing connectors. The housing holds layers of filter media 35 mm in diameter. The top layer 6 is a nonwoven fabric. Under this is a layer 8 of activated carbon/cellulose composite medium for methylene blue removal and up to four layers 10 of a nonwoven filter medium, which can be made from polypropylene, polyester, glass, and cellulose acetate components, for removal of-leukocytes and lipids, and for polishing filtration. In the filter used in the examples, the carbon/cellulose composite was Carbac 2640FH™, available from Cellulo Company [Cranford, N.J.] and the nonwoven filter for leukocytes was Type 825B from Lydall, Inc. [Hamptonville, N.C.]. The base of the cylindrical housing 1 has a spiral filtrate channel 12 to improve air removal and draining efficiency.

The filter device is connected at its inlet to a sealed, sterile-dockable tubing about 40 cm in length, and optionally a tubing clamp. The filter is connected from its outlet to a receiving blood bag with about 50 cm length of tubing. When the inlet tubing is sterile-docked to a supply bag of virally inactivated plasma, the distance measured from the midpoints of the supply and receiving bags is nominally 75 cm.

A unit of fresh-frozen plasma is thawed and brought to room temperature, and tare weighed. An aliquot of methylene blue solution is injected into the plasma corresponding to a final dye concentration of 0.1 $\mu$M (equivalent to 0.4 $\mu$g/mL). The plasma is mixed by manual agitation of the bag for about 30 seconds, and a sample is removed for analysis. This plasma supply bag is sterile-docked to the filter assembly via the clamped filter inlet tubing. The supply bag is hung on a stand, with the filter and supply bag suspended freely below. The tubing clamp is opened to start the flow of plasma. Total time for the entire unit of plasma to pass through the filter is monitored. The filtered plasma is sampled for analysis.

Examples of 1 to 10 utilized devices containing one layer of activated carbon filter and four layers of the nonwoven leukocyte filter; example 11 utilized two layers of leukocyte filter medium. Examples 1 to 4 illustrate methylene blue removal; examples 5 to 8 illustrate methylene blue removal and changes in coagulation factors before and after filtration; example 9 shows methylene blue removal and leukodepletion (equivalent to 99.94% removal); examples 10 and 11 show the effects of different filter configurations and plasma temperature variation on methylene blue removal and leukodepletion. For these tests pooled plasma was used immediately following thawing (temperature at start of filtration cycle was about 4° C.).

| Example | Plasma wt. (g) | Methylene blue concn. in filtered plasma ($\mu$g/mL) [a] | Filtration time (min) |
|---|---|---|---|
| 1 | 300 | <0.02 | 17.5 |
| 2 | 300 | <0.02 | 14.9 |
| 3 | 205 | <0.02 | 10.4 |
| 4 | 212 | <0.02 | 10.6 |
| 5 | 264 | <0.02 | 13.0 |
| 6 | 189 | <0.02 | 11.3 |
| 7 | 199 | <0.02 | 8.7 |
| 8 | 211 | <0.02 | 13.5 |
| 9 | 169 | <0.02 | 9.6 |
| 10 | 242 | <0.02 | 39.6 |
| 11 | 287 | <0.02 | 50.7 |

| | Change in coagulation factor content (%) | | | | | Leukodepletion performance | |
|---|---|---|---|---|---|---|---|
| Example | Fibrinogen | Factor V | VII | VIII | IX | XI | WBC count per mL before filtration | WBC count per mL after filtration [b] |
| 1 | | | | | | | | |
| 2 | | | | | | | | |
| 3 | | | | | | | | |
| 4 | | | | | | | | |
| 5 | −3 | 2 | 5 | −3 | −15 | −48 | | |
| 6 | 0 | −14 | 9 | −6 | −11 | −54 | | |
| 7 | 0 | −3 | 8 | −8 | −11 | −62 | | |
| 8 | −3 | 0 | 8 | −6 | −15 | −53 | | |
| 9 | | | | | | | 87800 | 50 |
| 10 | | | | | | | 7400 | 0 |
| 11 | | | | | | | 7400 | 0 |

[a]: 0.02 $\mu$g/mL is the limit of detection of methylene blue by HPLC
[b]: Nageotte method. (American Assoc. of Blood Banks Technical Manual; p 760; method 11.12)

We claim:

1. A method for removing leukocytes and one or more viral inactivating agents from whole blood or a blood fraction comprising:

passing said blood or blood fraction through a filter adapted for removing leukocytes and antiviral agents, said filter comprising a material capable of retaining leukocytes, and activated carbon capable of removing said viral inactivating agent.

2. A method for removing leukocytes and one or more viral inactivating agents according to claim 1, wherein said material capable of retaining leukocytes comprises a mechanically stable polymeric material.

3. A method according to claim 1 wherein said blood fraction is plasma.

4. A method according to claim 1 wherein said viral inactivating agent is selected from the group consisting of phenothiazine dyes and photo-decomposition products of phenothiazine dyes.

5. A method according to claim 4 wherein said viral inactivating agent is selected from the group consisting of methylene blue, toluidine blue, and photodecomposition products of methylene blue and toluidine blue.

6. A method according to claim 2, wherein said mechanically stable polymeric material is included within a laid textile web.

7. A method according to claim 1 comprising passing said blood or blood fraction sequentially through (1) a layer containing activated carbon and (2) at least one shape-sustaining laid textile web having a thickness of 1 to 8 mm and a bulk density of 0.05 to 0.4 g/cm$^3$, said web comprising:

(a) a plurality of interlocked textile fibers with average deniers between 0.05 and 0.75 and average lengths between 3 mm and 15 mm, said textile fibers being substantially uniformly distributed in said web so as to form a matrix of the textile fibers with spaces between adjacent interstices of interlocked fibers; and (b) a mechanically stable polymeric material comprising a plurality of fibrillated particles of polymeric material having a surface area of 5 to 60 square meters per gram substantially disposed within said spaces of the matrix, said fibrillated particles having a plurality of fine fibrils which are interlocked with adjacent textile fibers of said spaces such that the fibrillated particles are not substantially displaceable from said web during filtration of said blood.

8. A method according to claim 1 further characterized in that said filter additionally removes chylomicrons and lipids.

9. A method according to claim 1 further characterized in that said filter additionally removes microaggregates.

10. A method according to claim 1 further characterized in that said filter additionally removes bacteria.

11. A method according to claim 1 further characterized in that said filter additionally removes endotoxins.

12. A method for removing leukocytes and methylene blue from plasma comprising passing said plasma through a filter comprising (a) a material capable of retaining leukocytes and (b) activated carbon.

* * * * *